United States Patent [19] [11] 4,310,523
Neumann [45] Jan. 12, 1982

[54] COMBINED ANTIESTROGENS AND ANTIGONADOTROPICALLY EFFECTIVE ANTIANDROGENS FOR THE PROPHYLAXIS AND THERAPY OF HYPERPLASIA OF THE PROSTATE

[75] Inventor: Friedmund Neumann, Berlin, Fed. Rep. of Germany

[73] Assignee: Schering Aktiengesellschaft, Berlin and Bergkamen, Fed. Rep. of Germany

[21] Appl. No.: 195,812

[22] Filed: Oct. 10, 1980

Related U.S. Application Data

[63] Continuation-in-part of Ser. No. 28,745, Apr. 10, 1979, abandoned.

[30] Foreign Application Priority Data

Apr. 17, 1978 [DE] Fed. Rep. of Germany ....... 2817157

[51] Int. Cl.³ ..................... A01N 45/00; A61K 31/56
[52] U.S. Cl. .................................................. 424/240
[58] Field of Search ............. 260/397.5, 397.4, 397.46; 424/238, 230

[56] References Cited

U.S. PATENT DOCUMENTS 3,076,823  2/1963  Ringold et al. ................. 260/397.4
3,423,507  1/1969  Neri ..................................... 424/243
4,055,641  10/1977 Benson et al. ..................... 424/242

OTHER PUBLICATIONS

Chem. Abstracts (1978), vol. 89, Par. 197804g.

Primary Examiner—Elbert L. Roberts
Attorney, Agent, or Firm—Millen & White

[57] ABSTRACT

A pharmaceutical composition comprising an anti-estrogen and an antigonadotropically effective anti-androgen, e.g., in a weight ratio of anti-estrogen to anti-androgen of essentially 2:1 to 1:10 is effective for the prophylaxis and therapy of prostate hyperplasia. Suitable anti-estrogens include, for example, tamoxifen. Antigonadotropically active anti-androgens preferably are steroids having anti-androgenic and progestational properties, e.g., cyproterone acetate.

16 Claims, No Drawings

COMBINED ANTIESTROGENS AND ANTIGONADOTROPICALLY EFFECTIVE ANTIANDROGENS FOR THE PROPHYLAXIS AND THERAPY OF HYPERPLASIA OF THE PROSTATE

CROSS-REFERENCE TO RELATED APPLICATIONS

This application is a continuation-in-part of application Ser. No. 028,745, filed Apr. 10, 1979 now abandoned.

BACKGROUND OF THE INVENTION

The present invention relates to a new combination of drugs for the prophylaxis and therapy of prostate hyperplasia.

Prostate hyperplasia is a benign enlargement of the prostate beginning from the so-called "inner" prostate. The attendant complaints are due primarily to the resultant obstructions of the urethra. Voiding is made difficult and retention of urine residue occurs. Without surgical interference, uremia can ensue.

Heretofore, it has hardly been possible to medicinally treat this disease, occurring with great frequency in older men. The phyto-preparations tested for this purpose, e.g., $\beta$-sitosterol, mixtures of various plant extracts, and combinations of plant extracts with the neutropic spasmolytic azoniaspirochloride have proved ineffective as determined by a one-year study. Although the patients in this study experienced an improvement in miction symptoms, under therapy, an involution of the hyperplastic prostate was not achieved.

Hormones have likewise been utilized in the treatment of prostate hyperplasia. Among these compounds, the depot progestogen gestonorone caproate deserves particular mention. As compared to the phyto-preparations, a better effect is obtained with gestonorone caproate. The miction period, prolonged prior to treatment, is markedly shortened, and the maximum flow value (flow of urine per unit time) is improved. A marked reduction of the size of the adenoma, however, also cannot be achieved with this compound.

In U.S. Pat. No. 3,423,507, a treatment of prostate hypertrophy is described. It involves use of the progestationally and anti-androgenically effective esters of 6-chloro-17-hydroxy-1$\alpha$,2$\alpha$-methylenepregna-4,6-diene-3,20-dione (cyproterone esters). However, it was found that even under this treatment there is only a partial retrogression of hyperplasia.

In prostate hyperplasia, the fibromuscular proportion of the prostate (interstitium) proliferates primarily. A possible cause for this, inter alia, is a shift in the estrogen/androgen ratio in favor of the estrogens. It has been found in various investigations that, in older men, the serum testosterone concentrations are reduced; at the same time, the proportion of SHBG (sex hormone binding globuline, specific transport protein for steroids) increases, so that the biological availability of androgens is even further reduced.

In the conventional laboratory animal species, only older dogs experience spontaneous prostate hyperplasia comparable to the changes caused in males by prostate hyperplasia. Also in the dog, there is a proliferation primarily of the fibromuscular portion of the prostate. It is also possible to cause the aspects of the disease in younger dogs by treatment with an estrogen or an estrogen/androgen mixture. Our own experiments have shown that the additional treatment with anti-androgen (cyproterone acetate) leads to total atrophy of the gland parenchyma, but that the proliferation of the interstitium is not affected.

In autoradiographic studies on human prostate hyperplasia tissue, it has furthermore been shown that only the gland epithelium (parenchyma) is a target organ for androgens, rather than the interstitium. Additionally, it was discovered that fibroblast cultures from human prostata hyperplasia tissue aromatize testosterone about seven to nine times more strongly to estrogens than fibroblast cultures derived from healthy prostata tissue.

SUMMARY OF THE INVENTION

Accordingly, it is an object of this invention to provide a method and an agent for the human male which is effective to produce an involution of the epithelial as well as the fibromuscular portion of the prostate, whereby an increased secretion of androgens is also to be avoided.

It is an object of this invention to provide a method and an agent for the prophylaxis and treatment of prostate hyperplasia.

Upon further study of the specification and appended claims, further objects and advantages of this invention will become apparent to those skilled in the art.

These objects have been attained by the present invention by providing an agent, and a method of use thereof, comprising an anti-estrogen and an anti-androgen having an antigonadotropic effect, in a weight ratio of anti-estrogen to anti-androgen of essentially 2:1 to 1:10, preferably 2:1 to 1:2.

DETAILED DISCUSSION

Suitable anti-estrogens for use in accordance with this invention include all conventional anti-estrogens, both steroidal and non-steroidal. Examples of suitable non-steroidal anti-estrogens include:

tamoxifen = (Z)-2-[p-(1,2-diphenyl-1-butenyl)-phenoxy]-N,N-dimethylethylamine, nafoxidine = 1-(2-[4-(6-methoxy-2-phenyl-3,4-dihydro-1-naphthyl) phenoxy]-ethyl)-pyrrolidine, hydrochloride, MER25 = 1-[p-(2-diethylaminoethoxy)-phenyl]-2-(p-methoxyphenyl)-1-phenylethanol, TACE = tri-(p-anisolyl)-chloroethylene, clomiphene = 1-[p-($\beta$-diethylaminoethoxy)phenyl]-1,2-diphenylchloroethylene, cyclofenil = bis(p-acetoxyphenyl)cyclohexylidenemethane, and CI-628 = 1-(2-(p-[$\alpha$-(p-methoxyphenyl)-$\beta$-nitrostyryl]-phenoxy)-ethyl)-pyrrolidine.

Examples of suitable steroidal anti-estrogens include:

RU-16117 = 11$\alpha$-methoxy-17$\alpha$-ethynyl-1,3,5(10)-estratriene-3,17$\beta$-diol, and 16$\beta$-ethylestradiol = 16$\beta$-ethyl-1,3,5(10-estratriene-3,17$\beta$-diol.

The structures of the non-steroidal anti-estrogens are as follows:

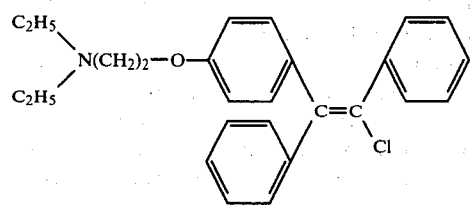

Clomiphene

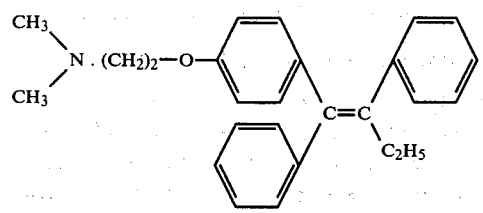

Tamoxifen

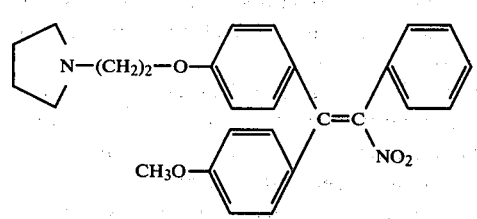

Cl-628

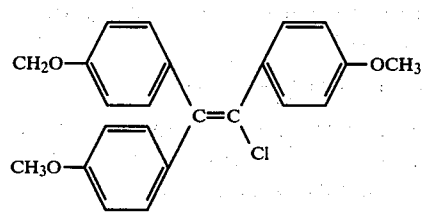

TACE

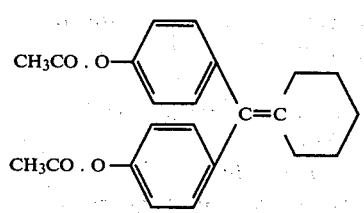

Cyclofenil

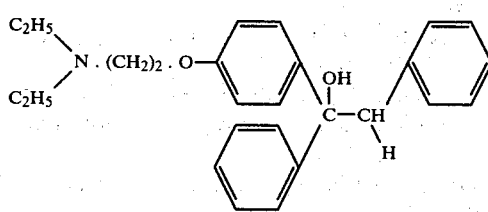

MER-25

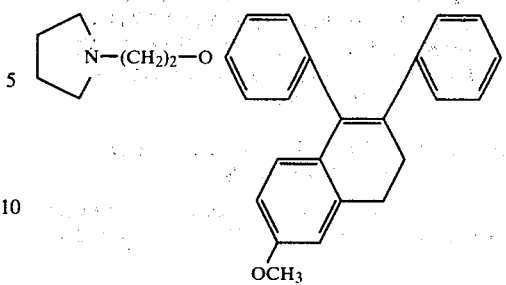

Nafoxidine

The structures of the steroidal antiestrogens are as follows:

RU-16117

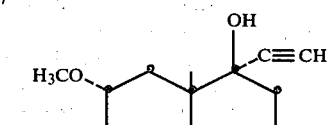

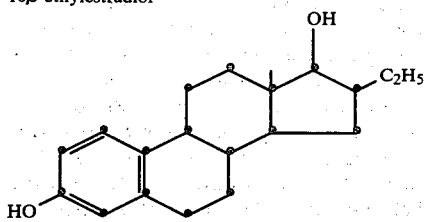

16β-ethylestradiol

As can be seen, antiestrogens equivalent to the examples listed above in general include substituted diphenylalkanes (non-steroidal) and substituted estradiols (steroidal). All such antiestrogens meeting the requirements set forth herein are, of course, within the scope of this invention.

The steroidal compounds are discussed, respectively, in Azadian-Boulanger et al, Eur. J. Med. Chem. 1978, 13(4), 313-9 or Raynaud et al, J. Steroid. Biochem., 1975, 6, 615-22, and Takikawa, Chem. Pharm. Bull., 1977, 25(3) 501-3, the disclosures of which are incorporated by reference herein. All of the exemplary antiestrogens mentioned above are discussed in Nishino, Gynäkologe 12, 199-211 (1979), whose disclosure is also entirely incorporated by reference herein.

In general, those anti-estrogens which have a spectrum of activity essentially the same as that of tamoxifen are employable in this invention, most notably, essentially the same spectrum of hormonal activity as tamoxifen. More particularly, since all known anti-estrogens also display estrogenous effects (depending on the dosage, duration of administration, host species, target organ, etc.), the anti-estrogens of the invention should have a ratio of anti-estrogenic activity to estrogenic activity which is about the same as or larger than that of tamoxifen. A description of the activity spectrum of tamoxifen is contained in, e.g., Drugs 16:1-24 (1978), all of whose disclosure is incorporated by reference herein.

For purposes of this application, the terms "essentially the same spectrum of (hormonal) activity" refers to the situation wherein two agents are effective for essentially the same purpose, i.e., possess essentially the same activities, but not necessarily with the same degree of effectiveness.

The relevant activity spectra and activities, e.g., estrogenic, antiestrogenic, endrogenic, gestagenic (see below), etc., can be determined by any of the conventional pharmaceutical protocols available for such purposes. Which particular ones are employed is not critical as long as both comparison agents are tested under the same conditions.

For example, estrogenous/antiestrogenous activities can be determined by the conventional sialic acid test and by determination of uteral and vaginal weight changes in mice and rats. See, for example, the mentioned Nishino reference, especially Tables 1 and 2 and FIG. 2, along with the accompanying disclosure. These tests can be conducted as follows (see also, U.S. Pat. No. 3,951,959, whose disclosure is incorporated by reference herein):

Female NMRI-strain mice weighing about 30 g are ovariectomized. Starting with the 10th day after castration, the animals receive the substance to be tested once daily for 3 days. The daily dose is dissolved in 0.1 ml of castor oil containing a small amount of benzyl benzoate. The solution to be tested is administered subcutaneously to 6 animals per each dose. On the fourth day after the treatments, the animals are sacrificed by decapitation and exsanguinated. Vagina and uterus are immediately excised and weighed into a test tube for hydrolysis. The determination of the sialic acid is conducted according to Svennerholm/Biochem. Biophys. Acta 24 (1957) 604/. The increase in the vagina and uterus organ weights in dependence on the dose, as well as the reduction on the sialic acid content are determined. Therefore is derived the relative effective strength of the compound to be tested compared to the standard, estradiol. As parameters of the estrogenic activity, the sialic acid concentration and the uterus and vagina organ weights are employed. Data obtained are subjected to regression analysis to test the regression and linearity of the dose-responsive curve.

Furthermore, the level of antiestrogenous activity can be ascertained by measuring one or more of the following non-limiting listing of effects of the agent, all of which reflect an interference with the usual effects of estrogens: the estrogen-induced proliferation and hornification of the vaginal epithelium of rats and mice are prevented; the estrogen-induced hypophysis hypertrophy in rats is inhibited; the uterotropic effect of effective estrogens is inhibited, for instance, the estrogen-stimulated uterus growth in rodents is inhibited; the estrogenous effect in the sialic acid test is eliminated (the estrogen-determined decrease in sialic acid concentration in the vagina of mice is eliminated); the estrogen-stimulated prolactin release in rats is inhibited; etc.

For example, antiestrogenic activity can be demonstrated by an agent's effect on the uterus growth test for estradiol as follows:

Daily for 3 days 0.03 μg of estradiol and measured dosages of the antiestrogen to be tested are simultaneously applied to castrated or infantile mice subcutaneously. The animals are killed on the fourth day, and the uteri are removed and weighed without contents (See Table 1). The same test is carried out on castrated or infantile rats using 0.1 μg of estradiol.

It is especially to be noted that the structures of the antiestrogens of this invention are not derived from those of compounds which possess an androgenic or gestagenic activity. Accordingly, they do not possess androgenic or gestagenic side-effects. The antiestrogens of this invention are believed to act by displacing estrogens from the active centers (receptors) in the host; on the other hand, for example, compounds possessing some level of antiestrogenic activity and also androgenic or gestagenic activity function via other significantly different mechanisms, e.g., by removal of androgen which gives results categorizable as antiestrogenic.

One example of compounds having possible antiestrogenic effects which are not included within the scope of this invention are those disclosed in U.S. Pat. No. 4,055,641 to Benson et al which are primarily anabolic androgens. For example, the compound preferred by Benson et al, 3,17-dioxoandrost-4-ene-19-al (Column 3, lines 67–68) was tested in the vaginal swab test of the castrated rat after subcutaneous application in a dosage of 1 mg. Hornification of the vaginal epitelium took place, demonstrating that 3,17-dioxo-androst-4-ene-19-al displays a strongly estrogenous effect. In addition, the compounds of Benson et al were tested on intact (not castrated) male animals or probands. These estrogenous substances acted on the prostate by removal of androgen, not by displacing estrogen as for the antiestrogens used in this invention. The difference between the antiestrogens acting through an antagonism to estrogen receptors, i.e., those used in this invention, and those which are primariy androgenic or gestogenic in activity with some simultaneous antiestrogenic effect is also discussed in Nishino, supra.

The lack of androgenous activity can be ascertained, e.g., by the levator ani/seminal vesicle test on rats and the lack of gestagenous activity, e.g., by the Clauberg test on rabbits. These tests are conducted as follows (see also, U.S. Pat. No. 3,994,937, whose disclosure is incorporated by reference herein):

ANABOLIC AND ANDROGENIC ACTIVITY

Six male rats weighing 90–100 g are castrated. Seven days after castration, subcutaneous injections are administered to each animal during a period of fourteen days. The total number of injections is twelve and each injection involves 0.3–0.1 mg, respectively. On the day after the last application, the animals are autopsied and the weights of the seminal vesicle, the prostate gland and the levator ani muscle are determined. The weights of the organs are calculated relative to 100 g of body weight.

From the weights of the organs, the average weight is determined for the six test animals as a function of each particular dose.

Employing this test, which is conducted in a slightly modified conventional manner [Hershberger, L. G.; Shipley, E.; Meyer, R. K.; Proc. Soc. Exp. Biol. (N.Y.) 83 (1953) 175] the following data are obtained. The anabolic activity is evidenced by the levator ani weight; and the adrogenic activity is evidenced both by the seminal vesicle weight and the prostate gland weight.

The highest values of organ weights which are obtainable by administration of the highest acceptable doses of the strongest known anabolic substance and of the strongest known androgenic substance, respectively, are about 70 mg musculas levator ani per 100 g body weight, and about 450 mg seminal vesicle per 100 g body weight.

PROGESTATIONAL ACTIVITY

The progestational activity can be determined by the Clauberg test on infantile spayed rabbits weighing 800 to 1000 grams. A daily dose of 5 μg of estradiol dissolved in 1 ml of sesame oil is subcutaneously administered over a period of six days. From the seventh to the eleventh day, measured dosages of the compound to be tested are administered subcutaneously. The compound is dissolved in a medium consisting of benzylbenzoate/castor oil (1:10). On the twelfth day, the animals are autopsied. The progestational transformation of the endometrium is rated by the McPhail scale (1=no effect; 4=complete transformation of the endometrium).

There is determined the minimum amount (Threshold Dose) of the tested compounds sufficient to achieve an adequate positive effect (McPhail=1.5).

Suitable anti-androgens having an antigonadotropic acitivty per this invention include preferably steroids having anti-androgenic and progestational properties and having the following Formula I or II:

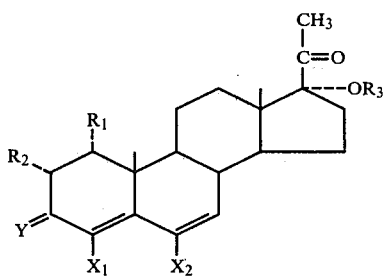

wherein
$R_1$ and $R_2$ are hydrogen or together form an additional carbon-to-carbon bond or methylene;
$R_3$ is a conventional acyl residue in accordance with conventional steroid chemistry;
Y is oxygen or the grouping (H, $OR_4$) wherein $R_4$ is hydrogen, acyl as defined above, or alkyl;
$X_1$ is hydrogen or chlorine; and
$X_2$ is hydrogen, fluorine, chlorine or alkyl; or

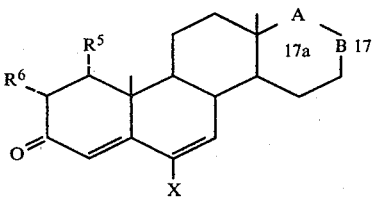

wherein
$R^5$ and $R^6$ are hydrogen or together are methylene;
X is hydrogen, fluorine or chlorine; and
A-B is

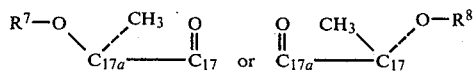

wherein $R^7$ and $R^8$ are a conventional acyl residue as defined above for Formula I.

Suitable acyl residues mentioned above include all such residues of the acids conventionally used in steroid chemistry for the esterification of secondary and tertiary hydroxy groups. Preferred such acyl groups are derived from aliphatic carboxylic acids of 1-8 carbon atoms, e.g., acetic acid, propionic acid, butyric acid, valeric acid, isovaleric acid, caproic acid, enanthic acid, etc. The esters of acetic acid (acetyl residues) are especially preferred. The many other conventional acyl groups are equivalents. Alkyl includes lower alkyl groups of 1-5 carbon atoms, the methyl group being preferred.

These compounds are fully conventional and are described, for example, in the following references: compounds of Formula I, for example, in U.S. Pat. Nos. 3,234,093; 3,076,823; 3,549,671; 3,789,087 and in British Pat. Nos. 890,315; 1,005,495; 1,049,026 and 1,172,086; and compounds of Formula II, for example, in U.S. Pat. No. 3,492,338, the disclosures of all of which are incorporated by reference herein.

Typical compounds of general Formula I include the 17-esters of, for example:
6-chloro-17-hydroxy-1α,2α-methylenepregna-4,6-diene-3,20-dione,
6-chloro-17-hydroxypregna-4,6-diene-3,20-dione,
6-chloro-17-hydroxypregna-1,4,6-triene-3,20-dione,
6-chloro-3ξ,17-dihydroxy-1α,2α-methylenpregna-4,6-dien-20-one,
6-chloro-3ξ-methoxy-17-hydroxy-1α,2α-methylenepregna-4,6-dien-20-one,
6-fluoro-17-hydroxy-1α,2α-methylenepregna-4,6-diene-3,20-dione,
17-hydroxy-1α,2α-methylenepregna-4,6-diene-3,20-dione and
4,6-dichloro-17-hydroxy-1α,2α-methylenepregna-4,6-diene-3,20-dione.

Preferred compounds of general Formula I include
6-chloro-17-hydroxy-1α,2α-methylenepregna-4,6-diene-3,20-dione acetate (cyproterone acetate) and
6-chloro-17-hydroxypregna-4,6-diene-3,20-dione acetate (chlormadinone acetate).

Typical compounds of general Formula II include, for example:
6-chloro-17aβ-acetoxy-17aα-methyl-1α,2α-methylene-D-homo-4,6-androstadiene-3,17-dione and
6-chloro-17α-acetoxy-17β-methyl-1α,2α-methylene-D-homo-4,6-androstadiene-3,17a-dione.

Anti-androgens having antigonadotropic effect which are not of Formula I or II, but which are equivalent to those which do have these formulae are included within the scope of this invention.

The anti-estrogens can be administered for this invention approximately in the same dosages at which the commercial anti-estrogens are employed, i.e., in daily dosages of about 5-100 mg, e.g., for tamoxifen. Similarly, the antigonadotropically active anti-androgens can be administered in amounts of about 5-100 mg per day.

The particular dosage for a given patient will vary according to conventional factors and according to the particular combination of compounds employed. For example, the dosages mentioned herein are typical for all named compounds but are especially suitable for the combination of cyproterone acetate and tamoxifen. Corresponding dosages for any other combination of suitable ingredients can be conventionally and routinely determined by simple experiments to determine the dosages which produce anti-androgenic and anti-estrogenic effects, respectively, which are equivalent to those produced by cyproterone acetate and tamoxifen at the mentioned dosages, e.g., using fully conventional pharmaceutical protocols, such as those mentioned herein.

The anti-estrogen and anti-androgen can be administered in a combined unitary form. They can also be administered separately in two different forms of administration in analogy to the separate conventional administration of each of the ingredients for conventional purposes.

The active agents can be processed into the customary forms of application for mammals, e.g., humans, using the additives, vehicles and/or flavor ameliorating agents customary in galenic pharmacy in accordance with conventional methods. For oral application, which is preferred, suitable particularly are tablets, dragees, capsules, pills, suspensions or solutions. Typical unit dosages of each ingredient are: anti-estrogen 5–50 mg, e.g., of tamoxifen; and anti-androgen 5–50 mg, e.g., of cyproterone acetate; with greater or lesser amounts being possible depending on the relative efficacy of a particular compound and the dosage desired for particular regimens.

Suitable for parenteral, especially intramuscular administration are oily solutions, e.g., sesame oil solutions or castor oil solutions. Typical unit dosages are: anti-estrogen 10–100 mg; and anti-androgen 10–100 mg, greater or lesser amounts being possible as described above. To increase solubility, it is also possible to add solubilizers, for example, benzyl benzoate or benzyl alcohol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

| Composition of a Tablet: | |
|---|---|
| 20.0 mg. | 6-chloro-17-hydroxy-1α,2α-methylenepregna-4,6-diene-3,20-dione acetate (cyproterone acetate) |
| 20.0 mg. | (Z)-2-[p-(1,2-diphenyl-1-butenyl)-phenoxy]-N,N-dimethylethylamine (tamoxifen) |
| 120.5 mg. | lactose |
| 59.5 mg. | corn starch |
| 2.5 mg. | poly-N-vinylpyrrolidone 25 |
| 2.0 mg. | "Aerosil" |
| 0.5 mg. | magnesium stearate |
| 225.0 mg. | total weight of the tablet which is produced in the usual way in a tablet press. |

Optionally, it is also possible to process cyproterone acetate and tamoxifen with respectively one-half of the aforementioned additives separately, and press a two-layer tablet.

EXAMPLE 2

| Composition of a Tablet: | |
|---|---|
| 10.0 mg. | 6-chloro-17-hydroxy-1α,2α-methylenepregna-4,6-diene-3,20-dione acetate (cyproterone acetate) |
| 10.0 mg. | (Z)-2-[p-(1,2-diphenyl-1-butenyl)-phenoxy]-N,N-dimethylethylamine (tamoxifen) |
| 130.5 mg. | lactose |
| 69.5 mg. | corn starch |
| 2.5 mg. | poly-N-vinylpyrrolidone 25 |
| 2.0 mg. | "Aerosil" |
| 0.5 mg. | magnesium stearate |
| 225.0 mg. | total weight of the tablet which is produced in the usual way in a tablet press. |

Optionally, cyproterone acetate and tamoxifen can also be pressed, with respectively one-half of the above-recited additives, separately into a two-layer tablet.

EXAMPLE 3

| Composition of an Oily Solution | |
|---|---|
| 50.0 mg. | cyproterone acetate |
| 50.0 mg. | tamoxifen |
| 353.4 mg. | castor oil |
| 618.6 mg. | benzyl benzoate |
| 1072.0 mg. | ≙ 1 ml. |

The solution is filled into an ampoule. Cyproterone acetate and tamoxifen can also be filled separately into two chambers, with respectively one-half of the above-mentioned additives.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

TABLE 1

Antiestrogenic Effect of Ru-16117 and Tamoxifen on the Estradiol-stimulated Uterus Weight of Infantile Mice
(Mode of Administration: Subcutaneous - Number of Animals per Group: Eight)
Ru-16117, Tamoxifen and Estradiol are dissolved in a medium consisting of benzylbenzoate/castor oil (1:10)

| | Ru-16117 | | Tamoxifen | |
|---|---|---|---|---|
| Dose over 3 Days (μg/Animal/Day) + 0.03 μg Estradiol/Animal/Day | Uterus Weight (mg) Average Value ± Standard Deviation | % Inhibition Decrease of Uterus Weight in Comparison to Single Estradiol Administration | Uterus Weight (mg) Average Value ± Standard Deviation | % Inhibition Decrease of Uterus Weight in Comparison to Single Estradiol Administration |
| 0.3 | 60.0 ± 2.4 | 8 | — | — |
| 3 | 49.8 ± 1.6 | 27 | 57.5 ± 2.1 | 11 |
| 30 | 34.3 ± 2.3 | 58 | 43.3 ± 3.1 | 40 |
| 100 | — | — | 39.7 ± 3.1 | 46 |
| 300 | — | — | 34.1 ± 4.3 | 58 |
| Single Administration of 0.03 μg Estradiol | 63.9 ± 6.2 | | | |

TABLE 1-continued

Antiestrogenic Effect of Ru-16117 and Tamoxifen on the Estradiol-stimulated Uterus Weight of Infantile Mice
(Mode of Administration: Subcutaneous - Number of Animals per Group: Eight)
Ru-16117, Tamoxifen and Estradiol are dissolved in a medium consisting of benzylbenzoate/castor oil (1:10)

| once Daily over 3 Days | |
|---|---|
| Untreated Control | 11.8 ± 1.3 |

As shown in Table 1 (above) Tamoxifen and Ru-16117 cause a similarly pronounced dosage-dependent decrease in uterus weight of the estradiol-stimulated uterus of infantile mice. Ru-16117 is somewhat more effective than Tamoxifen.

What is claimed is:

1. A pharmaceutical composition for the prophylaxis or treatment of prostate hyperplasia comprising an antiestrogen which is (Z)-2-[p-(1,2-diphenyl-1-butenyl)-phenoxy]-N,N-dimethylethylamine, 1-(2-[4-(6-methoxy-2-phenyl-3,4-dihydro-1-naphthyl)-phenoxy]-ethyl)-pyrrolidone hydrochloride, 1-[p-(2-diethylaminoethoxy)-phenyl]-2-(p-methoxyphenyl)-1-phenylethanol, tri-(p-anisolyl)-chloroethylene, 1-[p-($\beta$-diethylaminoethoxy)phenyl]-1,2-diphenylchloroethylene, bis(p-acetoxyphenyl)cyclohexylidenemethane, 1-[2-(p-[$\alpha$-(p-methoxyphenyl)-$\beta$-nitrostyryl]-phenoxy)-ethyl]-pyrrolidine, or 11$\alpha$-methoxy-17$\alpha$-ethynyl-1,3,5(10)-estratriene-3,17$\beta$-diol, and a antigonadotropically effective anti-androgen, in respective amounts such that the combination is effective for prophylaxis or treatment of prostate hyperplasia.

2. The composition of claim 1, further comprising a pharmaceutically acceptable carrier.

3. The composition of claim 1, wherein the weight ratio of anti-estrogen to anti-androgen is about 2:1–1:10.

4. The composition of claim 1, wherein the anti-estrogen is (Z)-2-[p-(1,2-diphenyl-1-butenyl)-phenoxy]-N,N-dimethylethylamine, 1-(2-[4-(6-methoxy-2-phenyl-3,4-dihydro-1-naphthyl)-phenoxy]-ethyl)-pyrrolidine hydrochloride, or 1-[p-(2-diethylaminoethoxy)-phenyl]-2-(p-methoxyphenyl)-1-phenylethanol.

5. The composition of claim 1 wherein (Z)-2-[p-(1,2-diphenyl-1-butenyl)-phenoxy]-N,N-dimethylethylamine is the anti-estrogen.

6. The composition of claim 1, wherein the anti-estrogen is 11$\alpha$-methoxy-17$\alpha$-ethynyl-1,3,5(10)-estratriene-3,17$\beta$-diol.

7. The composition of claim 1, wherein the antigonadotropically effective anti-androgen is a compound of the formula

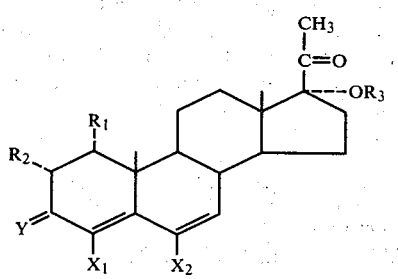

wherein $R_1$ and $R_2$ are hydrogen or together form an additional carbon-to-carbon bond or methylene;
$R_3$ is $C_{1-8}$ alkanoyl;
Y is oxygen or the grouping (H, OR$_4$) wherein R$_4$ is hydrogen, $C_{1-8}$ alkanoyl or $C_{1-5}$ alkyl;
$X_1$ is hydrogen or chlorine; and
$X_2$ is hydrogen, fluorine, chlorine or $C_{1-5}$ alkyl; or

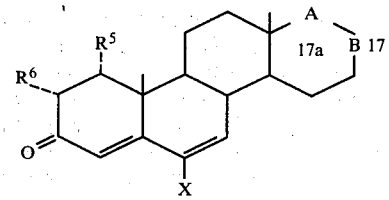

wherein
$R^5$ and $R^6$ are hydrogen or together are methylene;
X is hydrogen, fluorine or chlorine, and
A–B is

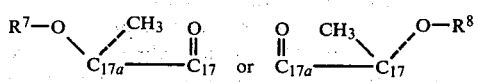

wherein $R^7$ and $R^8$ are each $C_{1-8}$ alkanoyl.

8. The composition of claim 7, wherein the antigonadtropically effective anti-androgen is 6-chloro-17-hydroxy-1$\alpha$,2$\alpha$-methylenepregna-4,6-diene-3,20-dione acetate.

9. The composition of claim 7, wherein the antigonadotropically effective anti-androgen is 6-chloro-17-hydroxypregna-4,6-diene-3,20-dione acetate.

10. The composition of claim 4, wherein the antigonadotropically effective anti-androgen is 6-chloro-17-hydroxy-1$\alpha$,2$\alpha$-methylenepregna-4,6-diene-3,20-dione acetate.

11. The composition of claim 4, wherein the antigonadotropically effective anti-androgen is 6-chloro-17-hydroxy-pregna-4,6-diene-3,20-dione acetate.

12. The compound of claim 5, wherein the antigonadotropically effective anti-androgen is 6-chloro-17-hydroxy-1$\alpha$,2$\alpha$-methylenepregna-4,6-diene-3,20-dione acetate.

13. A pharmaceutical composition of claim 2, comprising 5–50 mg of (Z)-2-[p-(1,2-diphenyl-1-butenyl)-phenoxy]-N,N-dimethylethylamine and 5–50 mg of 6-chloro-17-hydroxy-1$\alpha$,2$\alpha$-methylenepregna-4,6-diene-3,20-dione acetate, and the weight ratio of anti-estrogen to anti-androgen is about 2:1 to 1:10.

14. A method for prophylaxis or treatment of prostate hyperplasia which comprises administering an amount of a composition of claim 1 effective for the prophylaxis or treatment of prostate hyperplasia.

15. A method for prophylaxis or treatment of prostate hyperplasia which comprises administering an amount of a composition of claim 3 effective for the prophylaxis or treatment of prostate hyperplasia.

16. The method of claim 15, wherein the daily dosage of the anti-estrogen is 5–100 mg and the daily dosage of the anti-gonadotropically effective anti-androgen is 5–100 mg.

* * * * *